(12) United States Patent
Mittra et al.

(10) Patent No.: US 9,096,655 B2
(45) Date of Patent: Aug. 4, 2015

(54) METHOD FOR IN-VIVO BINDING OF CHROMATIN FRAGMENTS

(75) Inventors: Indraneel Mittra, New Delhi (IN); Rekha Mannemcherril Ramesan, Kerala (IN); Chandra Prakash Sharma, Kerala (IN); Gopichettipalayam Subbaratnam Bhuvaneshwar, Kerala (IN); Kavita Anirban Pal, Nagpur (IN)

(73) Assignee: TATA MEMORIAL CENTRE, Parel, Mumbai (IN)

(*) Notice: Subject to any disclaimer, the term of this patent is extended or adjusted under 35 U.S.C. 154(b) by 0 days.

(21) Appl. No.: 13/575,756

(22) PCT Filed: Jan. 24, 2011

(86) PCT No.: PCT/IN2011/000052
§ 371 (c)(1),
(2), (4) Date: Jul. 27, 2012

(87) PCT Pub. No.: WO2011/092715
PCT Pub. Date: Aug. 4, 2011

(65) Prior Publication Data
US 2012/0301487 A1    Nov. 29, 2012

(30) Foreign Application Priority Data
Jan. 27, 2010  (IN) .......................... 212/MUM/2010

(51) Int. Cl.
| | | |
|---|---|---|
| *A61K 47/28* | (2006.01) | |
| *A61K 39/44* | (2006.01) | |
| *C07K 16/08* | (2006.01) | |
| *A61K 47/48* | (2006.01) | |
| *A61K 39/00* | (2006.01) | |

(52) U.S. Cl.
CPC ............. *C07K 16/08* (2013.01); *A61K 47/4823* (2013.01); *A61K 2039/505* (2013.01)

(58) Field of Classification Search
CPC .................................................... C07K 16/303
See application file for complete search history.

(56) References Cited

U.S. PATENT DOCUMENTS

| | | | |
|---|---|---|---|
| 4,690,905 A | 9/1987 | Diamond | |
| 5,354,554 A | 10/1994 | Rhind | |
| 5,795,719 A | 8/1998 | Richard et al. | |
| 7,307,166 B1 | 12/2007 | Von Borstel et al. | |
| 7,541,028 B2 * | 6/2009 | Sung et al. ................. | 424/130.1 |
| 7,541,031 B2 | 6/2009 | Salfeld et al. | |
| 2007/0092509 A1 | 4/2007 | Mittra et al. | |
| 2008/0131954 A1 * | 6/2008 | Stone ............................ | 435/270 |
| 2010/0179303 A1 * | 7/2010 | Natarajan et al. ............. | 530/300 |

OTHER PUBLICATIONS

Drotleff et al., Eur. J. Pharm. and Biopharm. 2004, 58:385-407.*
Apoptosis and Autoimmunity from Mechanisms to Treatment, Edited by J.R. Kalden and M. Herrmann. Co. Wiley-Vch, Weinheim (2003), only contents and titles.
Badley AD, Pilon AA, Landay A, Lynch DH. Mechanisms of HIV-associated lymphocyte apoptosis. Blood,96:2951-64 (2000).
Barada FA Jr, Suratt PM, Davis JS 4th.et. al. Free plasma DNA in patients with pulmonary embolism. Southern Medical Journal. Mar. 1980;73(3):345-6, 350.
Bennett M.R. Apoptosis in the cardiovascular system. Heart 87, 480-487 (2002).
Benoit M, Fenollar F, Raoult D. et.al. Increased levels of circulating IL-16 and apoptosis markers are related to the activity of Whipple's disease. PLoS ONE. Jun. 6, 2007;2(6):e494.
Butt AN, Shalchi Z, Hamaoui K. et. al. Circulating nucleic acids and diabetic complications. Ann N Y Acad Sci. Sep. 2006;1075:258-70.
Chang CP, Chia RH, Wu TL. et. al. Elevated cell-free serum DNA detected in patients with myocardial infarction. Clinica Chimica Acta. Jan. 2003;327(1-2):95-101.
Dellinger EP, Anaya D.A Infectious and immunologic consequences of blood transfusion. Critical Care 8, S18-S23 (2004).
D'Intini V et. al. Longitudinal study of apoptosis in chronic uremic patients. Seminars in Dialysis, 16,467-73 (2003).
Fadeel, B., Orrenius, S., Zhivotovsky, B. Apoptosis in human disease: a new skin for the old ceremony. Biochem. Biophys. Res. Com. 266, 699-717 (1999).
Fliedner T.M., Graessle D, Paulsen C. & Reimers K. Structure and functions of bone marrow hemopoiesis: Mechanisms of response to ionizing radiation exposure. Cancer Biotherapy & Radiopharmaceuticals 17, 405-425 (2002).
Galeazzi M, Morozzi G, Piccini M. et. al. Dosage and characterization of circulating DNA: present usage and possible applications in systemic autoimmune disorders. Autoimmunity Reviews Jan. 2003;2(1 ):50-5.
Geiger S, Holdenrieder S, Stieber P. et. al. Nucleosomes in serum of patients with early cerebral stroke. Cerebrovascular Diseases 2006;21 (1-2)32-7.
Holdenrieder S, Eichhorn P, Beuers U. et. al. Nucleosomal DNA fragments in autoimmune diseases. Ann N Y Acad Sci. Sep. 2006;1075:318-27.
Holdenrieder S, Stieber P, Bodenmuller H. et. al. Nucleosomes in serum of patients with benign and malignant diseases. International Journal of Cancer. Mar. 20, 2001;95(2):114-20.

(Continued)

*Primary Examiner* — Gyan Chandra
(74) *Attorney, Agent, or Firm* — Pillsbury Winthrop Shaw Pittman LLP

(57) ABSTRACT

A process for substantially reducing levels of circulating chromatin fragments (CCFs) from a medium using binding agents such as antibodies or antibodies complexed with haemocompatible natural polymer substrates like as alginates, chitosan and pullulan to form complexed antibody-substrate nano-particulates (CNP) to bind and/or inactivate CCFs is disclosed. The amount of antibody bound to the polymer varies from 30% to 100% of activated sites in the polymer. Elevated levels of CCFs can be substantially reduced following administration of tissue damaging agents that generate apoptotic chromatin fragments by the concomitant administration of CNPs or concomitant administration of H4 antibody alone. A method of treatment is disclosed wherein therapeutic dose of CNPs, or H4 antibody alone, are administered systematically, or orally, in a delivery system to curb pathological conditions that are associated with increased burden of circulating chromatin fragments.

13 Claims, 11 Drawing Sheets

(56) References Cited

OTHER PUBLICATIONS

Hotchkiss HS et al. Apoptotic cell death in patients with sepsis, shock, and multiple organ dysfunction. Critical Care Medicine 27, 1230-1251(1999).
Jellinger K.A. Cell death mechanisms in neurodegeneration. Journal of Cellular and Molecular Medicine 5, 1-17 (2001).
Kirkwood T.B.L. Understanding the odd science of aging. Cell 120, 437-447 (2005).
Kremer A, Holdenrieder S, Stieber P. et. al. Nucleosomes in colorectal cancer patients during radiochemotherapy. Tumour Biology 2006;27(5):235-42.
Kremer A, Wilkowski R, Holdenrieder S. et. al. Nucleosomes in pancreatic cancer patients during radiochemotherapy. Tumour Biology Jan.-Feb. 2005;26(1):44-9.
Lam NY, Rainer TH, Chan LY. et. al. Time course of early and late changes in plasma DNA in trauma patients. Clinical Chemistry Aug. 2003;49(8): 1286-91.
Leon SA, Shapiro B, Sklaroff DM. et. al. Free DNA in the serum of cancer patients and the effect of therapy. Cancer Research Mar. 1977; 37(3):646-50.
Lombard D.B. et al. DNA repair, genome stability, and aging. Cell 120, 497-512 (2005).
Otton R, Soriano FG, Verlengia R, Curi R. Diabetes induces apoptosis in lymphocytes. Journal of Endocrinology 182, 145-56 (2004).
Parnaik, R., Raff, M.C. & Scholes, J. Differences between the clearance of apoptotic cells by professional and non-professional phagocytes. Current Biology 10, 857-860 (2000).
Rainer TH, Lam NY. Circulating nucleic acids and critical illness. Ann N Y Acad Sci. Sep. 2006;1075:271-7.
Saukkonen K, Lakkisto P, Pettila V. et. al. Cell-Free Plasma DNA as a Predictor of Outcome in Severe Sepsis and Septic Shock. Clinical Chemistry Apr. 17, 2008;54:1000-1007.
Williams, R.C., Malone, C.C., Meyers, C., Decker, P., Muller, S. Detection of nucleosome particles in· serum and plasma from patients with systemic lupus erythematosus using monoclonal antibody 4H7. The Journal of Rheumatology 28, 81-94 (2001).
Wyllie, A.H., Kerr, J.F.R., Currie, A.R. Cell death: the significance of apoptosis. International Review of Cytology 68, 251-306 (1980).
Zeerleder S, Zwart B, Wuillemin WA. et. al. Elevated nucleosome levels in systemic inflammation and sepsis. Critical Care Medicine. Jul. 2003;31(7):1947-1951.
Zhong XY, Gebhardt S, Hillermann R. et. al. Circulatory nucleosome levels are significantly increased in early and late-onset preeclampsia. Prenatal Diagnosis Aug. 2005; 25(8):700-3.
Forsberg et al. Differential effects of invasion by and phagocytosis of *Salmonella typhimurium* on apoptosis in human macrophages: potential role of Rho.GTPases and Akt. J. Leukoc. Biol. 2003, 74:620-629.

\* cited by examiner

Scheme of conjugating antibody to pullulan

Percentage of % of thiolated sites in pullulan bound to antibodies (AB) with increasing concentration of AB In vivo efficacy of the antibody-nanoparticles using BALB/c mice: Effect of single vs. multiple doses. Note : that the levels of CCFs increases dramatically only after 48 hours.

Survival of mice treated with LPS and LPS + CNPs

Enrichment factor calculated at various time points after LPS and LPS + CNPs treatment in mice (p<0.01)

Levels of Monocyte chemo-attractant protein 1 in LPS and LPS+ CNPs treated mice (p<0.0001)

Levels of Interferon γ in LPS and LPS+ CNPs treated mice (p<0.0001)

Levels of Tumor Necrosis Factor in LPS and LPS+ CNPs treated mice
($p<0.0001$)

Levels of Interleukin-12 in LPS and LPS+ CNPs treated mice (p<0.0001)

Levels of Interleukin-6 in LPS and LPS+ CNPs treated mice (p>0.05)

Levels of Interleukin-10 in LPS and LPS+ CNPs treated mice (p>0.05)

METHOD FOR IN-VIVO BINDING OF CHROMATIN FRAGMENTS

FIELD OF THE INVENTION

The invention relates to binding of chromatin fragments on substrates for substantially reducing levels of chromatin fragments from a medium that is minimally invasive using antibodies or antibodies complexed with biodegradable and low molecular weight polymers. The present invention further provides for a method to reduce the morbidity of diseases that are associated with elevated levels of circulating chromatin fragments CCFs such as cancer, systemic autoimmune disorders, diabetes, Parkinson's disease, Alzheimer's disease, cerebral stroke, myocardial infarction, inflammation, sepsis, critical illness, trauma, renal failure, HIV/AIDS, etc. as well as ageing and age-related disorders wherein the elevated levels of CCFs are removed from the body by binding/inactivating the chromatin fragments with antibodies or complexed antibody-substrate nano-particulates.

BACKGROUND OF THE INVENTION

Active cellular suicide or programmed cell death, also known as apoptosis, plays an important role in animal development, tissue homeostasis, immune response and a wide variety of pathological conditions including cancer, atherovascular diseases, diabetes, Alzheimer's disease, Parkinson's disease, stroke, severe infections, sepsis, renal failure, HIV/AIDS, autoimmune disorders etc. [Wyllie, A. H., Kerr, J. F. R., Currie, A. R. Cell death: the significance of apoptosis. Int. Rev. Cytol 68, 251-306 (1980); Fadeel, B., Orrenius, S., Zhivotovsky, B. Apoptosis in human disease: a new skin for the old ceremony. Biochem. *Biophys. Res. Com.* 266, 699-717 (1999)]. Apoptosis is characterized by programmed or systematic activation of a number of genes, especially those coding for caspases, which lead to cleavage of the chromatin/DNA into smaller fragments which are entrapped in apoptotic bodies that result from disintegration of the apoptotic cells. Under physiological conditions these apoptotic bodies and the chromatin/DNA contained within them are efficiently removed when ingested by macrophages.

Hundreds of billions of cells die in the body everyday and an equal number of cells are generated to replace them [Fliedner T. M., Graessle D, Paulsen C. & Reimers K. Structure and functions of bone marrow hemopoiesis: Mechanisms of response to ionizing radiation exposure. *Cancer Biotherapy & Radio pharmaceuticals* 17, 405-425 (2002)]. Unless these apoptotic cells are efficiently eliminated by phagocytosis, apoptotic chromatin/DNA can enter the blood stream from tissues and blood cells undergoing normal apoptotic turnover. Indeed, with the recent availability of a quantitative sandwich-enzyme-immunoassay which employs antibodies to both DNA and histones (Cell Death Detection ELISA$^{Plus}$, Roche Biochemicals), fragments of chromatin in the form of mono- and oligonucleosomes have been shown to be present in sera of normal persons, and in higher quantities in patients with cancer, systemic autoimmune disorders, diabete's, cerebral stroke, myocardial infarction, inflammation, sepsis, critical illness, trauma, pulmonary embolism, inflammatory bowel disease, organ transplantation and pre-eclampsia. Leon S , Shapiro B, Sklaroff D M. et. al. Free DNA in the serum of cancer patients and the effect of therapy. *Cancer Res.* 1977 March; 37(3):646-50; Holdenrieder S, Stieber P, Bodenmuller H. et. al. Nucleosomes in serum of patients with benign and malignant diseases. *Int J Cancer.* 2001 Mar. 20; 95(2):114-20; Kremer A, Wilkowski R, Holdenrieder S. et. al. Nucleosomes in pancreatic cancer patients during radio-chemotherapy. *Tumour Biol.* 2005 January-February; 26(1): 44-9; Kremer A, Holdenrieder S, Stieber P. et. al. Nucleosomes in colorectal cancer patients during radiochemotherapy. *Tumour Biol.* 2006; 27(5):235-42; Butt A N, Shalchi Z, Hamaoui K. et. al. Circulating nucleic acids and diabetic complications. *Ann NY Acad Sci.* 2006 September; 1075:258-70; Zeerleder S, Zwart B, Wuillemin W A. et. al. Elevated nucleosome levels in systemic inflammation 'and sepsis. *Crit Care Med.* 2003 July; 31(7):1947-51; Saukkonl: ln K, Lakkisto P, Pettila V. et. al. Cell-Free Plasma DNA as a Predictor of Outcome in Severe Sepsis and Septic Shock. Clin Chem. 2008 Apr. 17; Geiger S, Holdenrieder S, Stieber P. et. al. Nucleosomes in serum of patients with early cerebral stroke. Cerebrovasc Dis. 2006; 21 (1-2):32-7; Chang C P, Chia R H, Wu T L. et. al. Elevated cell-free serum DNA detected in patients with myocardial infarction. Clin Chim Acta. 2003 January; 327(1-2):95-1 01; Lam N Y, Rainer T H, Chan L Y. et.al. Time course of early and late changes in plasma DNA in trauma patients. Clin Chem. 2003 August; 49(8): 1286-91; Rainer T H, Lam N Y. Circulating nucleic acids and critical illness. Ann NY Acad Sci. 2006 September; 1075:271-7; Barada F A Jr, Suratt P M, Davis JS 4th. et. al. Free plasma DNA in patients with pulmonary embolism. South Med J. 1980. March; 73(3):345-6, 350; Galeazzi M, Morozzi G, Piccini M. et. al. Dosage and characterization of circulating DNA: present usage and possible applications in systemic autoimmune disorders. Autoimmun Rev. 2003 January; 2(1):50-5; Holdenrieder S, Eichhorn P, Beuers U. et. al. Nucleosomal DNA fragments in autoimmune diseases. Ann NY Acad Sci. 2006 September; 1075:318-27; Benoit M, Fenollar F, Raoult D. et.al. Increased levels of circulating IL-16 and apoptosis markers are related to the activity of Whipple's disease. PLoS ONE. 2007 Jun. 6; 2(6):e494; Zhong X Y, Gebhardt S, Hillermann R. et. al. Circulatory nucleosome levels are significantly increased in early and late-onset preeclampsia. Prenat Diagn. 2005 August; 25(8): 700-3.

It has been demonstrated that in patients with cancer, the elevated basal level of CCFs rises further following chemotherapy or radiotherapy within 24-72 hours [Holdenriedm, S. et al. Nucleosomes in serum of patients with benign and malignant diseases. Int J Cancer 95, 114-120 (2001)].

Blood component therapy/transfusion is a common therapeutic procedure. Since apoptotic chromatin fragments are known to circulate in blood of normal individuals, it is possible that during transfusion of blood or blood products such apoptotic chromatin fragments are transferred to the recipient leading to an increase in the burden of CCFs.

Apoptotic bodies can be ingested also by non-macrophage cells, such as fibroblasts, which are incapable of efficiently clearing them from the body. [Patnaik, R., Raff, M. C. & Scholes, J. Differences between the clearance of apoptotic cells by professional and non-professional phagocytes. *Curr. Biol.* 10, 857-860 (2000)]. When ingested by macrophages, the engulfed chromatin/DNA is known to be degraded and ultimately lost with the death of the scavenging cells. However, the fate of non-macrophage cells after they engulf the apoptotic chromatin fragments was unknown until recently.

It was recently shown that when CCFs purified from plasma/serum of normal subjects and patients suffering from different malignancies, both before and after chemo- or radiotherapy, are added to a variety of cells in culture, they freely enter the recipient cells without assistance and induce a DNA damage response (DDR) that is detectable within one hour. The DDR results in incorporation of exogenous chromatin into the host cell genomes. A DDR induced by chromatin fragments is observed in all cell types tested, including those of mesenchymal, epithelial, neuronal, endothelial, myocardial, hepatic and adipose tissue origin, as well as in isolated lymphocytes, suggesting that apoptotic chromatin may be an universal DNA damaging agent (I. Mittra, U. Samant, G. K. Modi, P. K. Mishra and G. S. Bhuvaneswar. A method for ex-vivo separation of apoptotic chromatin fragments from blood or plasma for prevention and treatment of diverse human diseases. US Patent Application No. FPAA819PCT dated Oct. 27, 2006).

When cells were exposed to purified CCFs, rapid onset of a sequence of morphological changes occurred in all cell types within a span of 7 days. The typical sequence included: cell cycle arrest→Increase in cell size→apoptosis→senescence of remaining cells. The PCCF treated cells showed numerous chromosomal aberrations as well as increase in size and number of centrosomes within 48 hours indicating the induction of chromosomal instability. By day 10, groups of rapidly proliferating, non-senescent cells with altered morphologies, some of which were apparently oncogenically transformed, arose and surrounded the senescent cells. When chromatin treated cells were injected into immuno-deficient mice, tumor development was observed in a proportion of the injected animals (I. Mittra, U. Samant, G. K. Modi, P. K. Mishra and G. S. Bhuvaneswar. A method for ex-vivo separation of apoptotic chromatin fragments from blood or plasma for prevention and treatment of diverse human diseases. US Patent Application No. FPAA819PCT dated Oct. 27, 2006).

When the effect of plasma was tested on cultured recipient cells and analysed by flow-cytometry using the apoptosis marker annexin V, induction of a much higher degree of apoptosis was seen in response to plasma obtained from patients suffering from diabetes, renal failure, sepsis and cancer, specially after chemo- or radiotherapy, compared to that induced by plasma from healthy subjects. When chromatin contained in plasma was removed by immuno-adsorption using anti-histone antibodies, the apoptosis inducing property of plasma was greatly attenuated (I. Mittra, U. Samant, G. K. Modi, P. K. Mishra and G. S. Bhuvaneswar. A method for ex-vivo separation of apoptotic chromatin fragments from blood or plasma for prevention and treatment of diverse human diseases. US Patent Application No. FPAA819PCT dated Oct. 27, 2006).

Progressive DNA damage leading to genomic instability, senescence and apoptosis of cells underlies human ageing [Kirkwood T. B. L. Understanding the odd science of aging. *Cell* 120, 437-447 (2005)]. Although free radicals generated within the body have been implicated as the DNA damaging agent related to ageing, this theory has not been satisfactorily substantiated [Lombard D.B. et al. DNA repair, genome stability, and aging Cell 120, 497-512 (2005)]. Increased DNA damage and apoptosis is also associated with a wide variety of age related degenerative diseases such as Alzheimer's disease, Parkinson's disease, Stroke, Atherovascular diseases, Diabetes etc. [Jellinger K. A. Cell death mechanisms in neurodegeneration. J Cell Mol Med 5, 1-17 (2001); Bennett M. R. Apoptosis in the cardiovascular system. Heart 87, 480-487 (2002); Otton R, Soriano F G, Verlengia R, Curi R. Diabetes induces apoptosis in lymphocytes. J Endocrinol 182, 145-56 (2004)].

Increased cellular apoptosis is also associated with inflammatory processes such as infections, sepsis, multi-organ system failure as well as autoimmune disorders [Hotchkiss H S et al. Apoptotic cell death in patients with sepsis, shock, and multiple organ dysfunction. Crit Care Med. 27, 1230-1251 (1999); Apoptosis and Autoimmunity from Mechanisms to Treatment, Edited by J. R. Kalden and M. Herrmann. Co. Wiley-Vch, Weinheim (2003);]. The above conditions are known to be associated with high circulating levels of apoptotic chromatin fragments in blood. [Zeerleder S et al. Elevated nucleosome levels in systemic inflammation and sepsis. Crit. Care Med. 31, 1947-1951 (2003) ; Williams, R. C., Malone, C. C., Meyers, C., Decker, P., Muller, S. Detection of nucleosome particles in serum and plasma from patients with systemic lupus erythematosus using monoclonal antibody 4H7. J Rheumatol 28, 81-94 (2001)]. It has been reported that renal failure is associated with an increased apoptotic turnover which may contribute to the high mortality in this condition. [D'Intini V et. al. Longitudinal study of apoptosis in chronic uremic patients. Semin Dial, 16,467-73 (2003); U.S. Renal Data System, USRDS 2005 Annual Data Report: Atlas of End-Stage Renal Disease in the United States, National Institute of Diabetes and Digestive and Kidney Diseases, Bethesda, Md., 2006]. HIV infection/AIDS is also associated with extremely high apoptotic turnover in CD4 positive cells and is causally related to the multiple pathological consequences/complications of this disease. [Badley A D, Pilon A A, Landay A, Lynch DH. Mechanisms of HIV-associated lymphocyte apoptosis. Blood,96:2951-64 (2000) ]. Blood and blood products, that are routinely transfused for diverse medical indications, are known to be associated with an array of adverse consequences [Dellinger E P, Anaya D. A Infectious and immunologic consequences of blood transfusion. Critical Care 8, S18-S23 (2004)]. Transfusion of blood or blood products can increase the apoptotic chromatin burden in the recipient by i) delivering the existing apoptotic chromatin in the donor blood/blood products, ii) delivering apoptotic chromatin fragments that are derived from cells that undergo apoptosis during storage and processing. This chromatin overload may have deleterious effects on the recipient.

Based on the above findings, an ex-vivo system for removal of CCFs was proposed for the prevention/treatment of pathological conditions associated with increased DNA damage, genomic instability, senescence, apoptosis and oncogenic transformation. Such an ex-vivo system may be used for the prevention/retardation of spread of cancer, systemic autoimmune disorders, diabetes, Parkinson's disease, Alzheimer's disease, cerebral stroke, myocardial infarction, inflammation, sepsis, critical illness, trauma, renal failure, HIV/AIDS, etc. as well as ageing and other age-related disorders. (I. Mittra, U. Samant, G. K. Modi, P. K. Mishra and G. S. Bhuvaneswar. A method for ex-vivo separation of apoptotic chromatin fragments from blood or plasma for prevention and treatment of diverse human diseases. US Patent Application No. FPAA819PCT dated Oct. 27, 2006).

A method of treatment for systemic lupus erythematosus (SLE) is described by Diamond et al. (U.S. Pat No. 4,690, 905). It uses monoclonal antibodies against anti-DNA antibodies and then using anti-idiotypic antibodies to remove the pathogenic anti-DNA antibodies from the patient's system. There are several drawbacks to this approach; it is dangerous to remove large quantities of blood from the patient. Removed blood has to be treated to remove the anti-DNA antibodies and then the treated blood is returned to the patient. It would be similar to hemodialysis, i.e., via an arterial passage. A risk of infection or the possible spreading of dangerous diseases such as HIV, hepatitis B, and hepatitis C is also there. Usage of nanoparticles avoids these problems.

High dose intravenous immune globulin (IVIG) infusions have also been used in treating certain autoimmune diseases. Previous studies have indicated that IVIG may contain anti-idiotype activity against anti-DNA antibodies, as well as many other autoantibodies (Jordan, S. C., 1989; Silvestris et al., 1994; Mouthon et al., 1996; Silvestris et al., 1996). The effects of IVIG infusions are apparently related to changes in the repertoire of autoantibodies expressed in the patient. This modulation of pathogenic Id antibodies is thought to depend on their specific interaction with the regulatory anti-idiotype molecules that occur naturally in healthy donors. Production of anti-idiotypic antibodies inhibiting the potentially harmful autoimmune repertoire may result from activation of the Id network committed to controlling the secretion of natural autoantibodies by CD5-positive B cells.

Treatment of SLE with IVIG has provided mixed results, including both resolution of lupus nephritis (Akashi et al., 1990), and in a few instances, exacerbation of proteinuria and kidney damage (Jordan et al., 1989). The cause of this increase is not clear but it is believed that there is increased glomerular deposition of immune-complexed, polyreactive, non-Id-specific IgG antibodies. Although there are several treatments for autoimmune disease such as SLE , all possess serious disadvantages.

SUMMARY OF THE INVENTION

Figure 1:
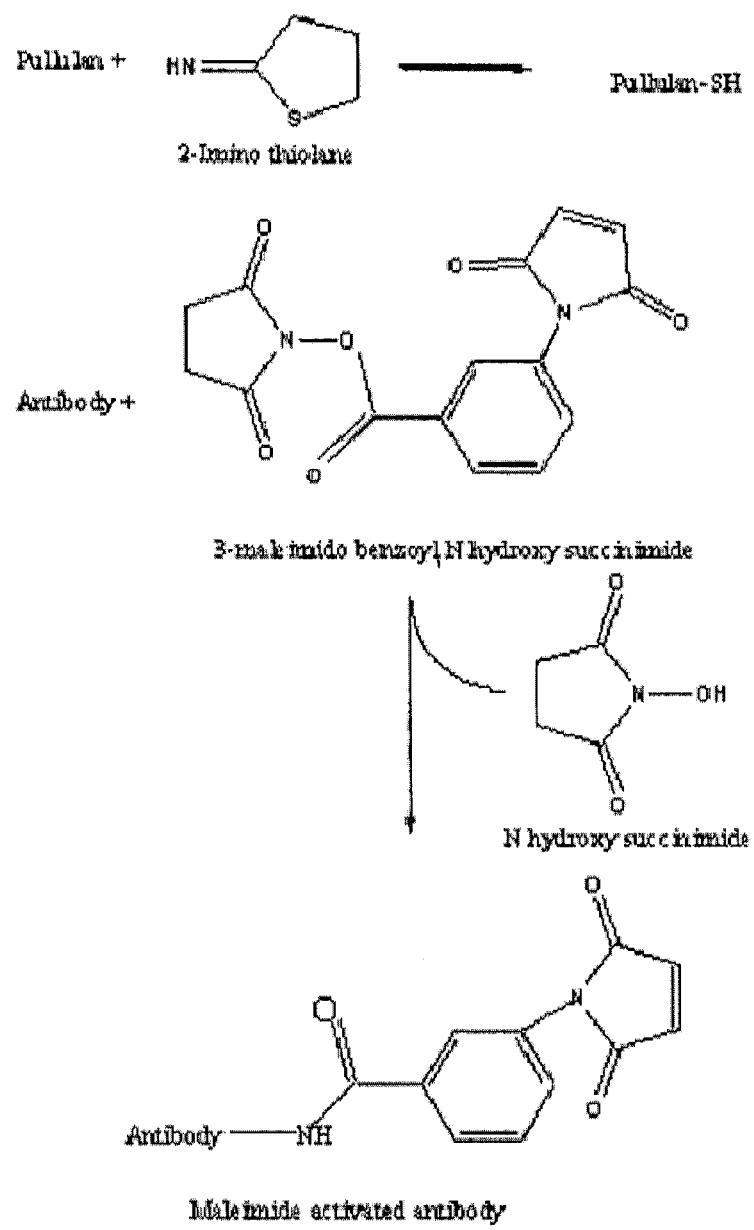
FIG. 1 Scheme of conjugating antibody to pullulan.

The main object of the invention is to provide means for removal of fragments of chromatin from a medium without requiring ex-vivo or extra corporeal treatment of blood/plasma.

Another object of the invention is to provide means for substantially reducing levels of fragments of chromatin from a medium that is minimally invasive with the use of binding agents such as antibodies.

Yet another object of the invention is to provide means for substantially reducing levels of fragments of chromatin from a medium that is minimally invasive using antibodies complexed with diverse substrates.

Yet another object of the invention is to provide a means for substantially reducing levels of fragments of chromatin from a medium that is minimally invasive using antibodies complexed with biodegradable and low molecular weight polymers.

Yet another object of the invention is to provide means for substantially reducing levels of fragments of chromatin from a medium with the use of complexed antibody-substrate nano-particulates (hereafter termed as "complexed nano particles" or "CNP")

Yet another object of the invention is to provide means for adsorbing and/or inactivating fragments of circulating chromatin in disease conditions associated with increased circulating chromatin burden.

Yet another object of the invention is to provide means for adsorbing and/or inactivating fragments of circulating chromatin for the nano-particulate-chromatin complex to be delivered to the liver for degradation.

Yet another object of the invention is to provide a means for reducing the level of chromatin in circulation.

Yet another object of the invention is to provide a method of treatment using the above means for adsorbing/inactivating fragments of circulating chromatin for therapeutic purposes in conditions like cancer, systemic autoimmune disorders, diabetes, cerebral stroke, myocardial infarction, inflammation, sepsis, critical illness, trauma, pulmonary embolism, inflammatory bowel disease, organ transplantation and pre-eclampsia and also to curb diverse pathological conditions that are associated with increased burden of CCFs.

Thus in accordance with this invention the process comprises:
  binding chromatin fragments with an antibody to enable the removal/substantially reduce level of the complex from circulation, or
  optionally selecting a polymer preferably with Asialo Glycoprotein Receptor (ASGPR) affinity, activating the polymer, activating an antibody, reacting the activated polymer and the activated antibody to form "polyplex" particles that can be further used for binding CCFs to aid their reduction and/or removal from circulation.

In an embodiment of the invention antibodies alone are used that act as efficient binding agents for chromatin and aid in their removal from circulation.

In another embodiment of the invention antibodies are complexed with natural polymers such as alginates, chitosan, pullulan and the like and testing of their efficacy in terms of removal of fragments of chromatin from circulation in adriamycin treated BALB/c mice and lipopolysacharide induced sepsis in C57B16 mice, wherein the chromatin levels are evaluated. Such elevated levels of fragments of chromatin may be achieved by agents that include chemotherapy drugs and agent causing tissue damage. The results indicate that such nano-particulate-antibody polymer complexes act as efficient binding agents for CCFs and aid in their removal from circulation. The reduction in CCFs levels is also demonstrated in adriamycin treated Balb C mice using anti-histone antibodies alone.

The present invention provides for a method to reduce the morbidity of diseases that are associated with elevated levels of CCFs such as cancer, systemic autoimmune disorders, diabetes, Parkinson's disease, Alzheimer's disease, cerebral stroke, myocardial infarction, inflammation, sepsis, critical illness, trauma, renal failure, HIV/AIDS, etc. as well as ageing and age-related disorders wherein the elevated levels of CCFs are removed from the body by binding/inactivating the chromatin fragments with antibodies or complexed antibody-substrate nano-particulates.

DETAILED DESCRIPTION OF THE INVENTION

The process of generating nanoparticles for the purpose of removal/inactivation of CCFs comprises activating the selected polymer by introducing reactive functional groups such as thiols, carboxyl or amino groups followed by purification, activating the amino groups in the antibody by introducing hetero-bifunctional cross-linking agents, complexing the activated polymer with the activated antibody and forming nano-particulates thereof, and binding CCFs with the said nano-particulates.

Optionally the CCFs are bound with selected antibodies alone. The scheme involving Pullulan is illustrated in FIG. 1. In the case of Pullulan, the hydroxyl groups are activated by introducing thiol functionality.

In the case of Chitosan, galactose is introduced into the amino groups by using lactobionic acid and (1-Ethyl-3-[3-dimethylaminopropyl]carbodiimide Hydrochloride) [EDC] and N-hydroxy succinimide [NHS] as the activating agents to obtain galacto-chitosan, quenched with hydroxylamine followed by introduction of thiol groups into the free amino groups as per the scheme:

$$\text{Chitosan} + \text{Lactobionic acid} \xrightarrow{\text{EDC, NHS 25° C., 24 hr}} \text{Galactosylated chitosan}$$

In another embodiment chitosan is activated with maleimide functional group by using 3-maleimido benzoic acid NHS ester followed by introducing the thiolated antibody onto the maleimide group as per FIG. 1.

The anti-histone antibodies, namely those against histones H1, H2A, H2B, H3 and H4, are activated using maleimide reactive groups present in hetero-bifunctional crosslinking agents at pH of 6.5-7.5 preferably at pH 7.0.

Complexing the activated polymer with the activated antibody and forming nano particulates is carried out by addition of the activated polymer to the activated antibody with stirring so as to avoid agglomeration thereby ensuring the formation of monodisperse nanoplexes.

The nanoplexes of less than 100 nm are preferred for efficient endocytosis.

These pullulan complexed nanoparticles were coded as PH1Np, PH2ANp, PH2BNp, PH3Np and PH4Np. All the five histone antibodies were taken at varying dose of 1 μg, 5 μg, 10 μg, 15 μg and 20 μg, activated and reacted with thiolated pullulan to get the individual antibody complexed nanoparticles. To obtain mixed nanoparticles (MNPs), the individual antibody complexed nanoparticles were mixed.

The chitosan nanoparticles were coded as CH1Np, CH2ANp, CH2BNp, CH3Np and CH4Np. All the five histone antibodies were taken at varying dose of 1 μg and 5 μg, activated and reacted with thiolated galacto chitosan to get the individual antibody complexed nanoparticles. To obtain mixed nanoparticles (MNPs), the individual antibody complexed nanoparticles were mixed. Antibodies against other chromatin proteins such as High Mobility Group Proteins may also be utilized for the purposes of complexing antibodies to substrates such as the polymers described above.

In a specific embodiment of the invention, nanoparticle complexes of natural polymers such as alginates, chitosan, pullulan, and cationic polymers etc with anti-histone antibodies have been prepared as potent substrates to bind with chromatin wherein galactose or mannose and thiol groups are introduced into the said polymers, as appropriate, based on the targeted application. The polymers are selected from those having Asialo Glycoprotein Receptor (ASGPR) affinity so that the liver targeting is achieved. Further the polymers are chosen from those that are haemocompatible. When cationic polymers are used, they are made to have ASGPR binding affinity and further need to be modified to become haemocompatible. The polymers such as chitosan and pullulan are preferably selected from those having molecular weights of 30000 to 100000 Dalton.

In-vivo Applications of Binding/Inactivating CCFs by CNPs

The binding/inactivation of CCFs can be used for therapeutic purposes in conditions like cancer, systemic autoimmune disorders, diabetes, cerebral stroke, myocardial infarction, inflammation, sepsis, critical illness, trauma, pulmonary embolism, inflammatory bowel disease, organ transplantation and pre-eclampsia and also to curb diverse pathological conditions that are associated with increased burden of CCFs.

CNPs can be administered systematically or orally in an appropriate delivery system. It is imperative that such CNPs need to be initially tested for their toxicity profile as well as for their pharmacokinetic profiles.

The successful binding/inactivation of CNPs in circulation can be ascertained by measuring the level of CCFs using the Death Detection ELISA (CDDE) kit (Roche). The latter is a sandwich ELISA system that simultaneously utilizes antibodies against histones and DNA, thereby having the capacity to effectively detect the presence of chromatin fragments.

The theraupetic dose of CNPs is determined by titrating the amount of CNPs that are required to be administered to substantially reduce the level of CCFs to barely detectable or undetectable levels.

After administering NCPs, the amelioration of disease symptoms as well as changes in appropriate biomarkers are monitored.

Determining Therapeutic Efficacy of CNPs

In order to determine the therapeutic efficacy of CNPs, experimentally induced sepsis is preferably chosen as a model system.

Lipo-polysaccride (LPS) is used to induce sepsis in mice. CNPs are administered concomitantly with LPS treatment. LPS-induced increase in levels of CCFs (if any) is measured using CDDE Kit with and without CNPs treatment.

Surprisingly, it has been found that LPS administration results in a marked increase in levels of CCFs. It was also surprisingly found that concomitant administration of CNPs results in a marked reduction in the levels of CCFs.

Further surprisingly, the levels of some inflammatory markers resulting from LPS induced sepsis were markedly reduced by the concomitant administration of CNPs.

LPS treatment in mice resulted in death of about 50% of the mice.

Surprisingly, the concomitant administration of CNPs prevented many of the deaths such that only about 30% of the mice died.

In-vivo Applications of Binding/Inactivating CCFs by H4 Antibody Alone

As indicated earlier, it has been surprisingly found that H4 antibody administered alone causes a dramatic reduction in elevated CCFs levels induced by adriamycin treatment in mice.

Since both CNPs and H4 antibody alone cause reduction in CCFs levels, and since the former is therapeutically effective in sepsis, H4 antibody alone can be used for therapeutic purposes in conditions like cancer, systemic autoimmune disorders, diabetes, cerebral stroke, myocardial infarction, inflammation, sepsis, critical illness, trauma, pulmonary embolism, inflammatory bowel disease, organ transplantation and pre-eclampsia and also to curb diverse pathological conditions that are associated with increased burden of CCFs.

The invention is now illustrated with non-limiting examples.

Examples 1-8 illustrate the preparation of CNPs. Example 9 and 10 illustrate the in-vitro and in-vivo efficacy of CNPs to bind chromatin. Example 11 illustrates the therapeutic efficacy of CNPs.

EXAMPLE 1

Activation of Pullulan

Pullulan (2%) was dissolved in 100 mL of borax (20 mM); pH of the reaction medium was maintained between 8 to 12 and 25 mg of Traut's reagent (2-iminothiolane) was added under stirring and the pH was adjusted to neutral (6.8 to 7.2) using 0.1 N HCl. The resultant solution was dialyzed against 0.1 M sodium phosphate, 0.15 M NaCl, pH 7.4 containing 1 mM EDTA to obtain the thiolated polymer (activated polymer). Polymers modified in such manner are effective in covalently cross linking antibodies.

EXAMPLE 2

Estimation of Thiolation of Activated Pullulan by Ellman's Assay

Ellman's reagent, 5-5', dithio-bis-(2-nitro benzoic acid) is used for determination of sulfydryls in proteins and other molecules. Ellman's reagent at concentration of 4 mg/mL in 0.1 M sodium phosphate (pH-8) was used for determination of sulfydryl concentration of the activated polymer by comparison to the standard curve using cysteine. It was seen that 50.61% of total pullulan to taken, was thiolated (activated) using Traut's reagent.

EXAMPLE 3

Synthesis of Galacto-Chitosan

Galactosylation of chitosan was achieved for its liver targeting using lactobionic acid. Galactosylation results in decrease in amine groups present in chitosan. Chitosan solution (2%) was prepared in 100 ml 0.2 N HCl. The pH of this solution was adjusted to 6.5 using 2 N NaOH under vigorous stirring. To this lactobionic acid was added (0.5 g in 10 ml distilled water) along with EDC and the pH was maintained at 6.5. The reaction was continued for 16 hours, dialyzed against distilled water for a day with two changes of water to obtain galacto-chitosan.

EXAMPLE 4

Estimation of Galactosylation

This was performed using 2, 4, 6-trinitrobnzenesulfonate (TNBS). Molecules containing primary amine or hydrazide groups react with TNBS to form a highly chromogenic derivative with absorbance maximum at 335 nm. This assay gives an indirect proof of decrease in amine group i.e. is equivalent to replacement of amine group with that of galactose. With the above amount of lactobionic acid, 25% of galctosylation was achieved.

EXAMPLE 5

Activation of Galacto-chitosan

To 25 ml of galactosylated-chitosan solution (1%) 12 mg of Traut's reagent was added under stirring and the pH was adjusted to 7.0 using 0.5 N NaOH. The reaction was maintained for one hour at room temperature. The resultant solution was dialyzed against 0.1 M sodium phosphate, 0.15 M NaCl, pH 7.4 containing 1 mM EDTA to obtain the thiolated polymer (activated polymer).

EXAMPLE 6

Estimation of Thiolation of Activated Galacto Chitosan by Ellman's Assay

The amount of thiolation of galacto-chitosan was measured using Ellman's reagent as performed for estimation of thiolation in activated pullulan. It was observed that 42.35% of thiolation was achieved using 12 mg of Traut's reagent.

EXAMPLE 7

Activation of Antibody

The antibodies were activated using 3-maleimido benzoyl NHS (MBS). 100 μl solution of the antibodies Anti-Histone H1, Anti- Histone H2A, Anti-Histone H2B, Anti-Histone H3 and Anti-Histone H4 at a concentration of 200 μg/ml was taken into labeled micro centrifuge tubes. MBS (5 μg) was added to the antibody and kept for half an hour at 25° C. till the reaction reached completion.

EXAMPLE 8

Synthesis of CNPs

The activated antibodies to histones namely, H1, H2A, H2B, H3 and H4 were mixed with the activated polymer, in this case thiolated (activated) polymers; pullulan or galactosylated chitosan in weight ratio of 1:100 to 1:200 for the complexation to take place. The activated polymer was added drop wise to the activated antibody under stirring at 25° C. to avoid aggregation and the formation of monodisperse nanoplexes. This series of antibody-nanoparticles were coded as H1Np, H2ANp, H2BNp, H3Np and H4Np. The five histone antibodies were activated individually and reacted with thiolated pullulan at a dose of 1 μg each, to get the mixed antibody nanoparticle viz., MNp.

1. Estimation of Particle Size of CNPs

The particle size of PH1Np, PH2ANp, PH2BNp, PH3Np and PH4Np was measured using Nanosizer (Malvern, UK) as given in table 1.

2. Estimation of Saturation Concentration of Ab Complexed to Activated Pullulan

Figure 2:
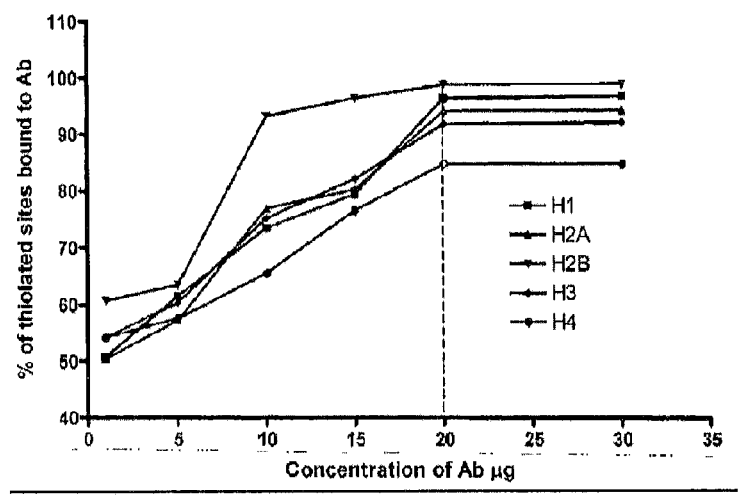
FIG. 2 Percentage of % of thiolated sites in pullulan bound to antibodies (AB) with increasing concentration of AB.

The activated antibodies to histones namely, H1, H2A, H2B, H3 and H4 were mixed with the activated polymer at varying concentration of Abs keeping pululan concentration constant. The activated polymer at 100 μL (2 mg) was added drop wise to the activated antibody (varying concentrations of 1, 5, 10, 15, 20 and 30 μg) the under stirring at 25° C. to avoid aggregation and the formation of monodisperse nanoplexes. This series of antibody-nanoparticles were coded as PH1Np, PH2ANp, PH2BNp, PH3Np and PH4Np. FIG. 2 shows that the saturation of all the thiolated sites on Pululan-SH (50.63% thiolated) was achieved at the antibody concentration of 20 μg.

Similarly, in case of thiolated galacto-chitosan (42. 5% thiolated), 100% binding of Abs was achieved at 20 μg of Abs.

EXAMPLE 9

1. In vitro Efficacy Evaluation of the Antibody Nanoparticles using L929 Cell Lines:

L929 cells, derived from an immortalized mouse fibroblast cell line, are internationally recognized cells that are routinely used in in vitro cytotoxicity assessments. In the present study, these cells were used to evaluate the efficacy of the prepared nano particulates to bind chromatin in a medium. The L929 cells were treated with adriamycin leading to the generation of apoptotic chromatin fragments. The cells were seeded in triplicate in Modified Eagles Medium (MEM) containing 10% foetal bovine serum in a 24 well cell culture plate at a concentration of $10^4$ cells/well. Cells were treated with adriamycin 2.5 µg/ml in MEM for 4 hours at 37° C. and placed in a $CO_2$ incubator. Similar Adriamycin treated cells were also exposed simultaneously to antibody-nanoparticles such that each well contained 5 µg of antibody per 100 micro litre of PBS. Five different antibody-nano particles were tested, namely H1Np, H2ANp, H2BNp, H3Np and H4Np. After 4 hours, the cells with and without nano-particulates exposure were lysed with cell lysis buffer, centrifuged at 200×g for 10 minutes and the supernatant was analyzed for concentration of chromatin fragments using Cell Death Detection ELISA$^{P\text{-}LUS}$ kit (Roche). Cells were also seeded in triplicate that was not treated either with adriamycin or with nano-particulates. The volume of reagents in each well is given in table 2.

2. In vitro Efficacy Evaluation of the Antibody Nanoparticles using B16F10 Cell Lines:

A lung metastatic subline of murine B16 melanoma cells, namely, B16-F10, was selected for another in vitro experiment in which B16F10 melanoma cells were treated with adriamycin (2.5 µg/mL) leading to the generation of apoptotic chromatin fragments in the culture medium. The cells were seeded in triplicate in Modified Eagles Medium (MEM) containing 10% foetal bovine serum in a 24 well cell culture plate at a concentration of $10^4$ cells/well. The adriamycin treated cells were either exposed to antibody-nanoparticles, namely, PH1Np, PH2ANp, PH2BNp, PH3Np, PH4Np and MNPs at varying concentrations or were not exposed to antibody-nanoparticles. After 24 hours, the cells with and without nano-particulates exposure were collected, centrifuged at 200×g for 5 minutes and the supernatant was analyzed for concentration of chromatin fragments using Cell Death Detection ELISA$^{PLUS}$ kit (Roche). The results with L929 and B16F10 cells were expressed in terms of chromatin enrichment factor calculated using the formula:

$$\text{Enrichment factor (control)} = \frac{\text{adriamycin}^+ CNPs^- \text{cells}}{\text{adriamycin}^- CNPs^- \text{cells}}$$

$$\text{Enrichment factor (experimental)} = \frac{\text{adriamycin}^+ CNPs^+ \text{cells}}{\text{adriamycin}^- CNPs^- \text{cells}}$$

The results for Chitosan (CH) and Pullulan (PH) Ab complexes as individual nanoparticles using adriamycin treated L929 cells are given in table 3. The results for Pullulan-Ab complexed nanoparticles both with individual Abs as well as in mixed nanoparticles using adriamycin treated B16F10 cells are shown in table 4. Both tables 3 and 4 show that the histone antibody labeled nanoparticles were efficient in binding chromatin fragments derived from apoptotic cells.

EXAMPLE 10

1. In vivo Efficacy Evaluation of Antibody-nanoparticles using BALB/c Mice

Six week old male BALB/c mice were used for these experiments and divided into those treated with adriamycin, those treated with adriamycin plus nanoparticles and those treated with PBS. Adriamycin was administered intraperitoneally to a group of five animals at a dose of 0.75 mg/mice. In the nanoparticle plus adriamycin treated animals, six groups of five animals each were maintained and treated as follows: Adriamycin+H1Np, Adriamycin+H2ANp, Adriamycin+H2BNp, Adriamycin+H3Np, Adriamycin+H4Np, and Adriamycin+MNp (M=mixture of all five antibody-nanoparticles). The antibody-nanoparticles were administered traperitoneally 40 hours after adriamycin treatment at an antibody concentration of 1 µg/animal. Finally, the last group of five animals received PBS treatment.

Blood samples were collected from mice by retro-orbital bleeding. An initial blood sample was collected from adriamycin treated mice at 40 hours, immediately prior to antibody-nanoparticle treatment. A second sample was withdrawn 4.5 hours after antibody-nanoparticle treatment in the relevant groups. Blood was collected in heparinised tubes. Plasma was collected by centrifugation. Chromatin levels detected using Cell Death Detection ELISA$^{PLUS}$ kit (Roche). Enrichment of chromatin released into circulation calculated using the formula $$\text{Enrichment factor (control)} = \frac{\text{adriamycin}^+ CNPs^- \text{animals}}{\text{adriamycin}^- CNPs^- \text{animals}}$$

$$\text{Enrichment factor (experimental)} = \frac{\text{adriamycin}^+ CNPs^+ \text{animals}}{\text{adriamycin}^- CNPs^- \text{animals}}$$

The values of the denominator were obtained in the same animals prior to adriamycin treatment. Table 4 shows the in vivo efficacy of antibody-nanoparticles in reducing CCFs levels in BALB/c mice expressed as enrichment factor. Table 5 represents percent reduction in enrichment factor with each antibody-nanoparticle used.

2. Effect of Single vs. Multiple Doses.

The study involved three groups of animals. Animals in group 1 received adriamycin followed immediately by a single dose of a mixture of all five antibody-nanoparticles. Group 2 received adriamycin followed by a mixture of antibody-nanoparticles immediately and every 24 hours thereafter for 4 days. Group 3 received adriamycin alone. Blood samples were collected from mice by retro-orbital bleeding before adriamycin dosing and also the blood samples were collected every 24 hours in heparinised tubes. Plasma was collected by centrifuging. Enrichment of chromatin released into circulation calculated using the formula $$\text{Enrichment factor (control)} = \frac{\text{adriamycin}^+ \text{single } CNPs^+ \text{animals}}{\text{adriamycin}^- CNPs^- \text{animals}}$$

$$\text{Enrichment factor (experimental)} = \frac{\text{adriamycin}^+ \text{multiple } CNPs^+ \text{animals}}{\text{adriamycin}^- CNPs^- \text{animals}}$$

Figure 3:
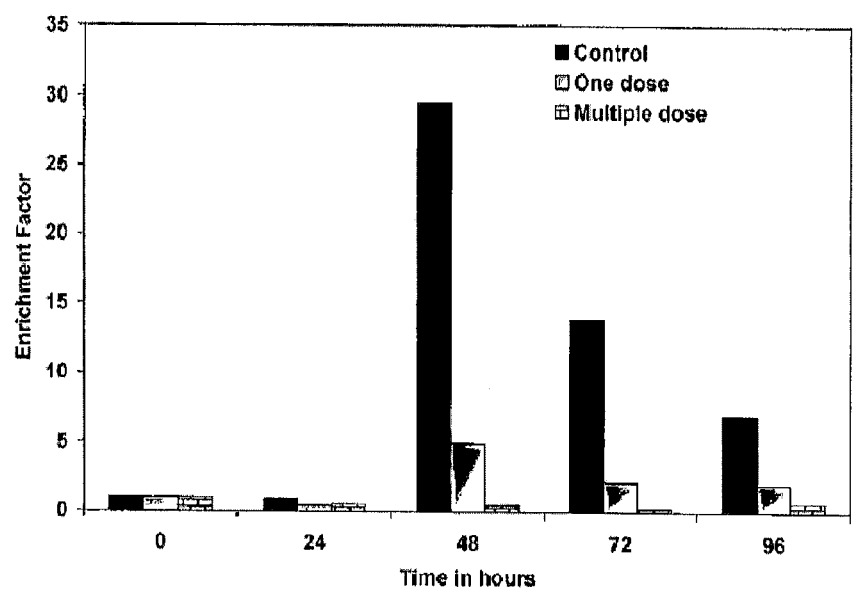
FIG. 3 In vivo efficacy of the antibody-nanoparticles using BALB/c mice: Effect of single vs. multiple doses. Note: that the levels of CCFs increases dramatically only after 48 hours.

The values of the denominator were obtained in the same animals prior to adriamycin treatment. It can be seen from FIG. 3 that levels of CCFs increases dramatically only after 48 hours. The FIG. 3 also shows that the effect of a single dose in reducing CCFs persists for the subsequent 48 hours although multiple dose treatment was more effective.

3. In vivo Efficacy Evaluation of H4 Antibody Alone using BALB/c Mice

Histone (H4) antibody alone was also tested in vivo for investigating its chromatin removal efficacy in comparison with the PH4Np. The experiment was conducted exactly as described for the in-vivo antibody-nanoparticle experiments described above. The concentration of antibody administered was 2.5 µg/per animal. It was observed that the antibody alone was also capable of reducing the level of CCFs. Table 6 shows that antibody alone against histone H4 alone is efficient in reducing the level of CCFs being almost as effective as nanoparticle-antibody H4.

Table 7 shows in vivo efficacy of antibody against histone H4 alone in reducing CCFs levels in BALB/c mice as compared to that achieved by anibody-nanoparticle H4 expressed in terms of enrichment factor.

EXAMPLE 11

1. Prevention of Fatality in Mice Receiving a Single Injection of LPS (20 mg/Kg) and Once Daily Infection of CNPs (10 µg of each Ab).
2. Induction of Sepsis in C57/ BL6 Mice by Lipopolysaccchride (LPS)

Sepsis was induced in C57/BL6 mice by LPS derived from *Salmonella enterica* serotype thyphimurium (Sigma, USA) administered intra-peritoneally as single injection.

3. Determination of LD50 of LPS

LPS at the doses of 20 mg/Kg, 25 mg/Kg and 30 mg/Kg were evaluated first for determination of LD50 in C57/BL6 mice (male, 7 to 8 weeks old) by intra peritoneal injection. Each dose group included three mice. It was observed that 3/3 mice died within 18 h of dosing LPS at 25 mg/Kg and 30mg/Kg, whereas in 20mg/Kg group 1/3 was found dead in 24 h time period. Therefore, this dose (20 mg/Kg) was chosen for further studies.

4. Monitoring Toxicity of CNPs in Mice

CNPs were administered to investigate whether symptoms of LPS-induced sepsis could be ameliorated by simultaneous injection of CNPs. First, the toxicity of CNPs in C57/BL6 mice was evaluated. The study comprised of three groups of mice. Group 1: administered CNPs at 1 µg of each Ab; group 2: administered CNPs at 5 µg of each Ab; group 3: administered CNPs at 10 µg of each Ab. Each group comprised of 5 mice. The nanoparticles were administered intra-peritoneally once daily for three days. Mortality (if any) was recorded at various time points (6 h, 18 h, 24 h, 36 h, 48 h and 60 h). It was observed that there was no mortality in all the doses tested. Therefore, the highest dose of CNPs i.e. 10 µg of each Ab was selected for further studies.

5. Monitoring Fatality of Mice given LPS and LPS+CNPs

Figure 4:
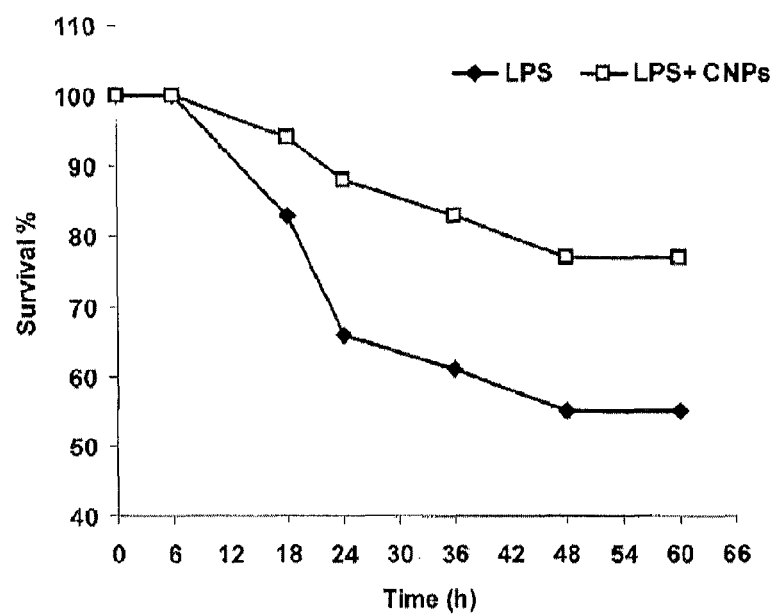
FIG. 4 Survival of mice treated with LPS and LPS+CNPs.

The experiment was performed in two groups of 18 C57BL6 mice each. Group 1was treated with LPS at 20 mg/Kg on day 0, and group 2 was treated with LPS and CNPs at a dose of 10 µg of each Ab once daily for three days. Both LPS and CNPs were administered intra-peritoneally. Fatality was recorded at various time points and survival curves were constructed. FIG. 4 shows the survival curves of mice of group 1 (LPS) and group 2 (LPS+CNPs). The survival of mice in the LPS group was 55% whereas that in the LPS+CNPs group was substantially better at 77% at 60 hrs.

6. Collection of Blood from Mice

Blood was collected from mice receiving LPS and LPS+CNPs from retro orbital plexus at different time points (6 h, 18 h, 24 h, 36 h, 48 h and 60 h) for estimation of CCFs and inflammatory markers in serum. Serum was separated after allowing blood to clot either at room temperature without centrifugation (for estimation of CCFs) or at 4° C. followed by centrifugation at 1200 g for 10 min. at 4° C. for estimation of inflammatory markers.

7. Estimation of CCFs Levels in Serum of Mice

The level of CCFs in serum was estimated using Cell Death Detection ELISA (CDDE) kit (Roche). This is a sandwich ELISA system that simultaneously utilizes antibodies to histones and DNA and specifically measures the level of chromatin in a solution. CCFs levels in serum were expressed in terms of enrichment factor which was calculated as follows:

$$\text{Enrichment factor (positive control)} = \frac{\text{Absorbance at 405 nm for } LPS^+ CNPs^- \text{serum}}{\text{Absorbance at 405 nm for } LPS^- CNPs^- \text{serum}}$$

$$\text{Enrichment factor (Test)} = \frac{\text{Absorbance at 405 nm for } LPS^+ CNPs^+ \text{serum}}{\text{Absorbance at 405 nm for } LPS^- CNPs^- \text{serum}}$$

Figure 5:
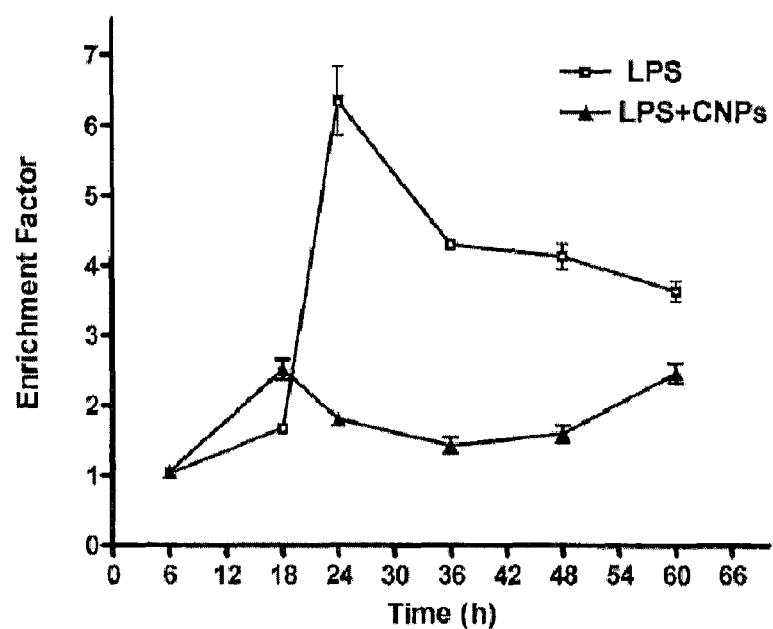
FIG. 5 Enrichment factor calculated at various time points after LPS and LPS+CNPs treatment in mice ($p<0.01$)
Figure 6:
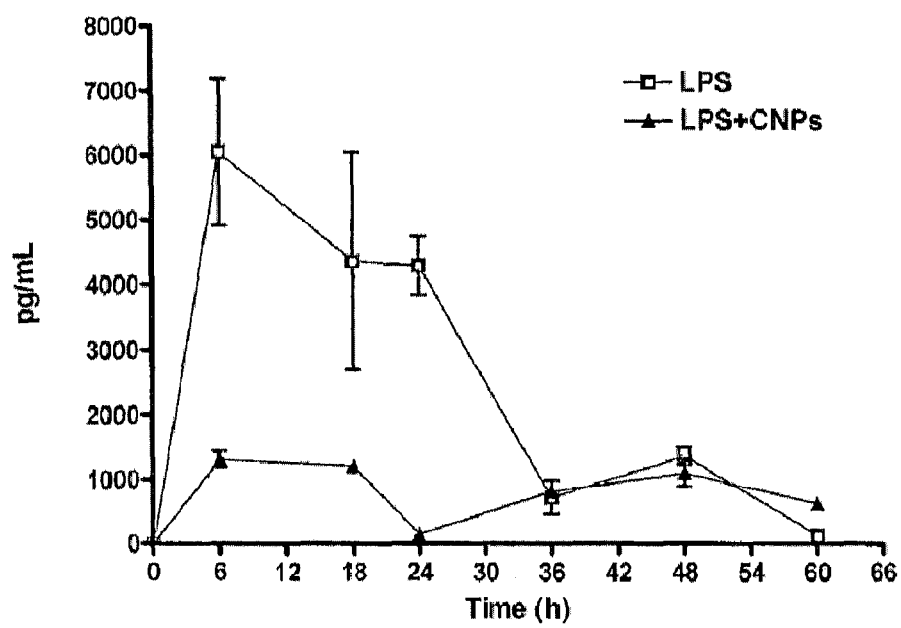
FIG. 6 Levels of Monocyte chemo-attractant protein 1 in LPS and LPS+CNPs treated mice ($p<0.0001$)
Figure 7:
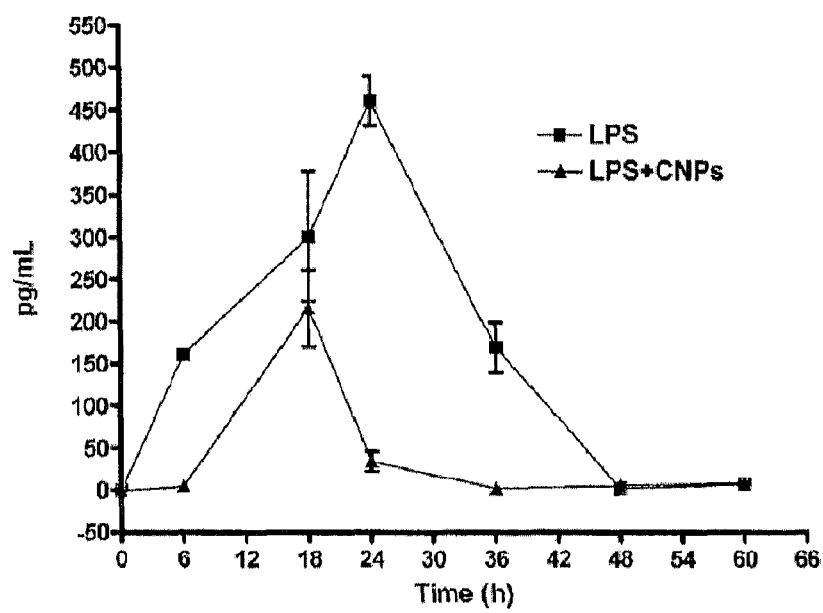
FIG. 7 Levels of Interferon γ in LPS and LPS+CNPs treated mice ($p<0.0001$)
Figure 8:
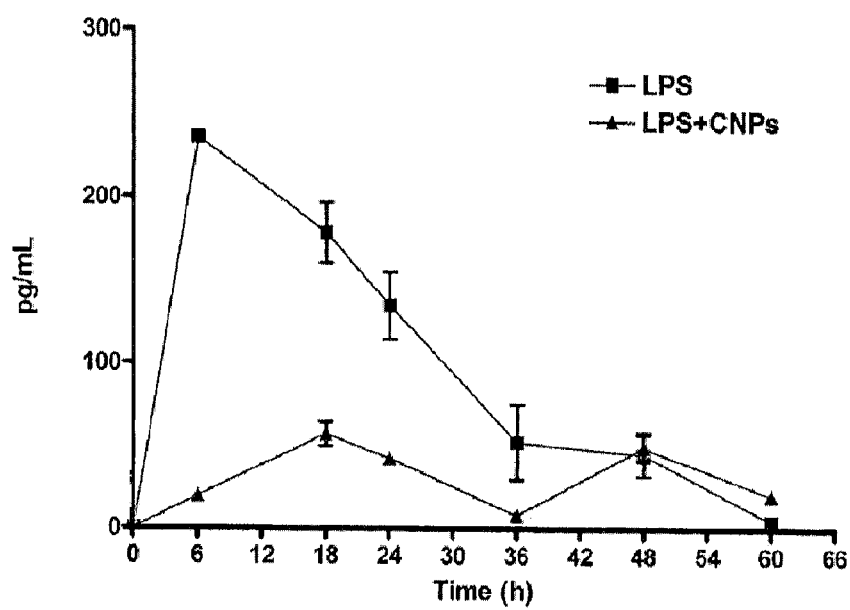
FIG. 8 Levels of Tumor Necrosis Factor in LPS and LPS+ CNPs treated mice ($p<0.0001$)
Figure 9:
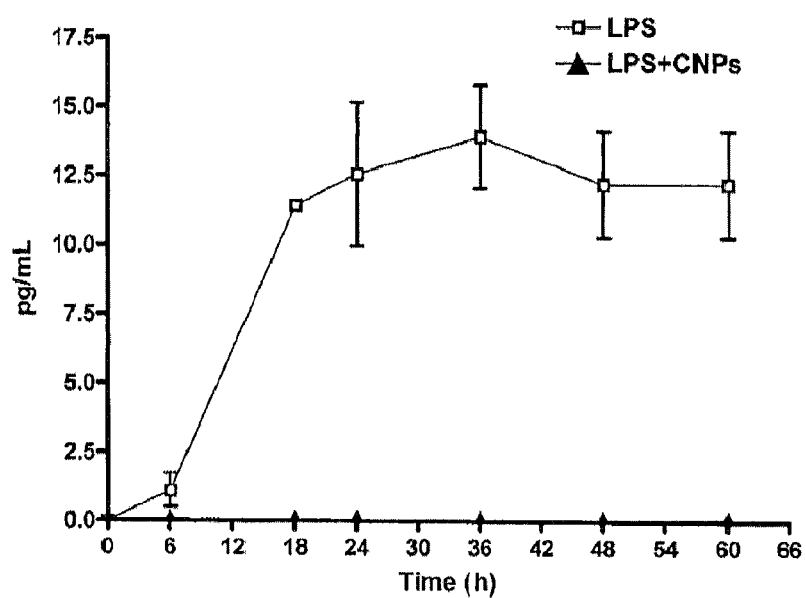
FIG. 9 Levels of Interleukin-12 in LPS and LPS+CNPs treated mice ($p<0.0001$)
Figure 10:
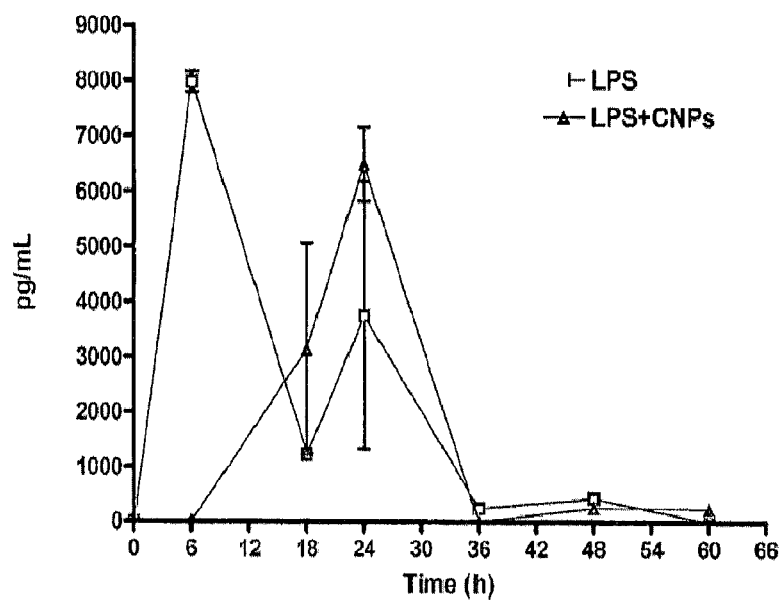
FIG. 10 Levels of Interleukin-6 in LPS and LPS+CNPs treated mice ($p>0.05$)
Figure 11:
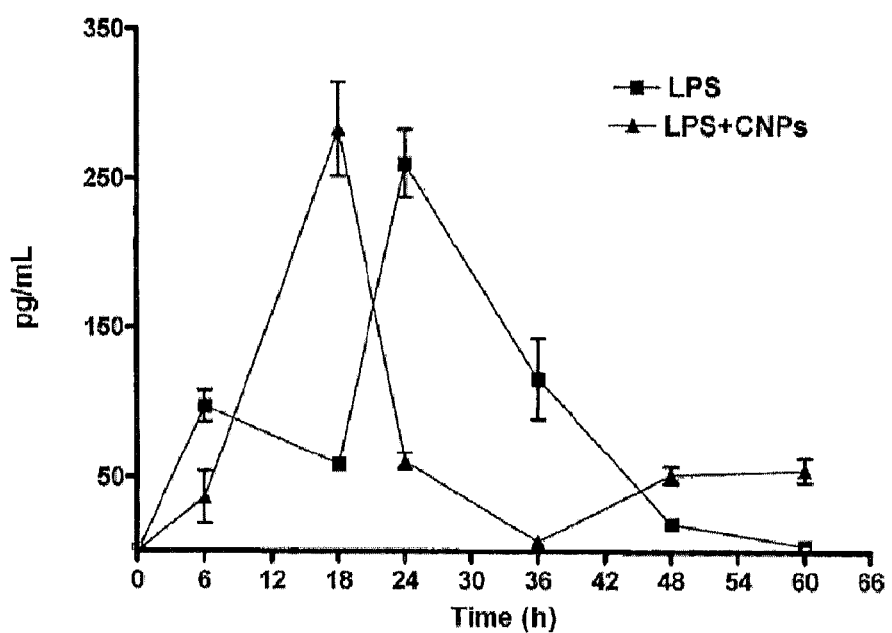
FIG. 11 Levels of Interleukin-10 in LPS and LPS+CNPs treated mice ($p>0.05$).

The values of the denominator were obtained in the same animals prior to LPS injection. FIG. 5 shows the enrichment factor at various time points in the two treatment groups. It is clearly seen that LPS injection caused a dramatic rise of CCFs levels which was most marked at 24 hrs. The simultaneous injection of CNPs with LPS caused a marked suppression of CCFs levels ($p<0.01$).

8. Estimation of Inflammatory Markers in Serum of Mice

Various inflammatory markers viz. monocyte chemoattarctant protein 1 (MCP 1), Interferon γ (IFN γ), Tumor Necrosis Factor (TNF a), Interleukin 12p70 (IL-12p70), Interleukin 6 (IL-6) and Interleukin 10 (IL-10) in serum were estimated using BD™ Cytometric Bead Array Mouse Inflammation Kit (BD Biosciences, USA).

FIGS. 6-11 shows that LPS treatment caused a marked rise in the various inflammatory markers and that this rise was significantly attenuated in case of MCP 1, IFNγ, TNFα and IL-12 ($p<0.0001$ for each). No significant suppression resulting from CNP treatment was observed in case of IL-6 and IL-10 ($p>0.05$).

Conclusion

A process for substantially reducing levels of circulating chromatin fragments (CCFs) from a medium using binding agents such as antibodies or antibodies complexed with haemocompatible natural polymer substrates like as alginates, chitosan and pullulan to form complexed antibody-substrate nano-particulates (CNP) to bind and/or inactivate CCFs is disclosed. The amount of antibody bound to the polymer varies from 30% to 100% of activated sites in the polymer. Elevated levels of CCFs can be substantially reduced following administration of tissue damaging agents that generate apoptotic chromatin fragments by the concomitant administration of CNPs or concomitant administration of H4 antibody alone. A method of treatment is disclosed wherein therapeutic dose of CNPs, or H4 antibody alone, are administered systematically, or orally, in a delivery system to curb pathological conditions that are associated with increased burden of circulating chromatin fragments

We claim:

1. A method for substantially reducing levels of circulating chromatin fragments (CCFs) from a medium of a mammal in need thereof, comprising introducing into the medium a nanoparticle comprising (a) a polymer having a selective affinity to liver of said mammal, and (b) an antibody that binds CCFs, wherein the antibody is covalently bound to the polymer.

2. The method of claim 1, wherein the nanoparticles are monodisperse nanoplexes <100 nm in size.

3. The method of claim 1, wherein the polymer comprises biodegradable low molecular weight polymers.

4. The method of claim 1, wherein the polymer comprises natural polymers having molecular weights of 30000 to 100000 Daltons.

5. The method of claim 1, wherein the polymers is haemocompatible.

6. The method of claim 1, wherein the polymers comprises alginates, chitosan or pullulan.

7. The method of claim 6, wherein the Chitosan comprises galactose or maleimide functional groups.

8. The method of claim 1, wherein the antibody comprises anti-histone antibodies selected from the group of those against histones H1, H2A, H2B, H3 and H4; and those producing antibodies against other chromatin proteins comprising High Mobility Group Proteins.

9. The method of claim 1, wherein the antibody comprises anti-histone antibodies against histones H1, H2A, H2B, H3 and H4, said anti-histone antibodies being activated by maleimide reactive groups present in hetero-bifunctional crosslinking agents at pH of 6.5-7.5.

10. The method of claim 1, wherein 30% to 100% of activated sites in the polymer are bound with the antibody.

11. The method of claim 1, further comprising introducing a tissue damaging agent that generates apoptotic chromatin fragments into the mammal, wherein the tissue damaging agent comprises adriamycin.

12. The method of claim 1 further comprising introducing lipopolysaccharide (LPS) into the mammal.

13. A method of treatment of cancer, systemic autoimmune disorders, diabetes, cerebral stroke, myocardial infarction, inflammation, sepsis, critical illness, trauma, pulmonary embolism, inflammatory bowel disease, organ transplantation or pre-eclampsia, the method comprising:

reducing circulating chromatin fragments (CCFs) from a delivery system of a mammal in need thereof by systematically or orally administering a therapeutic dose of a nanoparticle into the delivery system, wherein the nanoparticle comprises: a) a polymer having a selective affinity to Liver of the mammal, and (b) an antibody that binds CCFs; wherein the antibody is covalently bound to the polymer.

* * * * *